United States Patent [19]
Navaz

[11] Patent Number: 5,689,214
[45] Date of Patent: Nov. 18, 1997

[54] ELECTROMAGNETIC WAVE GENERATOR FOR INFLUENCING BIOMAGNETIC FIELDS

[75] Inventor: Juan Oses Navaz, Pamplona, Spain

[73] Assignee: Psycho Chrono, S.L., Pamplona, Spain

[21] Appl. No.: 559,028

[22] Filed: Nov. 16, 1995

[30] Foreign Application Priority Data

Jun. 8, 1995 [ES] Spain ................... 9501554 U

[51] Int. Cl.$^6$ ................... H03B 5/36; H04B 1/034
[52] U.S. Cl. ................... 331/158; 331/64; 331/74; 331/108 C; 331/179; 455/100; 455/129; 323/911
[58] Field of Search ................... 331/18, 64, 68, 331/74, 77, 108 C, 116 R, 116 FE, 158, 179; 455/95, 100, 118, 128, 129; 323/911

[56] References Cited

U.S. PATENT DOCUMENTS

| | | | |
|---|---|---|---|
| 1,598,862 | 9/1926 | Hangl | 323/911 X |
| 2,073,428 | 3/1937 | Schmid | 323/911 X |
| 4,101,871 | 7/1978 | Oliveira, II | 455/128 X |
| 4,211,980 | 7/1980 | Stowell | 455/100 |
| 4,366,482 | 12/1982 | Remes et al. | 455/95 X |
| 4,725,827 | 2/1988 | Gallegos, Jr. et al. | 455/95 X |
| 4,952,913 | 8/1990 | Pauley et al. | 455/100 X |
| 5,339,051 | 8/1994 | Koehler et al. | 331/158 X |
| 5,477,365 | 12/1995 | Knestel | 455/100 X |
| 5,512,879 | 4/1996 | Stokes | 455/100 X |

*Primary Examiner*—David Mis
*Attorney, Agent, or Firm*—Gary M. Nath; Nath & Associates

[57] ABSTRACT

An electromagnetic wave generator for influencing different corporal states in a biological organism includes an oscillator circuit coupled to a microcontroller and an antenna coupled to the microcontroller through which waves at a given frequency are transmitted to a biological organism.

3 Claims, 1 Drawing Sheet

ELECTROMAGNETIC WAVE GENERATOR FOR INFLUENCING BIOMAGNETIC FIELDS

BACKGROUND OF THE INVENTION

Research in biological medicine has shown that all the operations of the human organism are accompanied by bioelectrical phenomena, and it may be affirmed that the cells within the organism are directed in electromagnetic form and that different moods correspond to given frequencies in the brain cells.

Likewise, it has been proven that the electromagnetic function inside the body's cells is directly influenced by the biomagnetic fields that surround them, which allows the determination that, using well defined magnetic fields, it is possible to modify the electromagnetic state of the body, in order to originate the stimulation of moods as wished.

In this sense, this invention proposes a generator of waves at given frequencies, suitable for creating influences capable of providing different corporal states, in order to achieve, for example, greater relaxation during rest or greater dynamics for some activity.

SUMMARY OF THE INVENTION

This wave generator that is the subject of the invention basically consists of an oscillator circuit that generates the microcontroller's clock frequency, which generates the waves that are selected by means of user selectable contacts. The microcontroller provides a specific signal according to the selection, to give rise to the emission of waves through a coil in terms of a transmitting antenna.

Thus a device is obtained which is capable of generating a series of frequencies, any of which may be selected, for the creation of the magnetic influence desired by the user.

Said device has a minimum consumption, since it only requires a three volt pile or battery to supply operation; in addition, the size is very small, so that it may be placed for use on any piece of furniture, such as, for example, the night table beside the bed, or it may be carried in a pocket in the clothing, to be used wherever and whenever desired.

The field of influence of the device may vary in terms of the antenna employed, which, according to a preferred execution, is anticipated as being a small size in relation to the whole of the device, being capable a generating a field of influence in a spatial volume of between one and two cubic meters, which obviously is more than enough for the mentioned forms of application.

The device that is the subject of the invention therefore has very advantageous characteristics that confer on it a life of its own and a preferred character for the mentioned function of adapting the corporal state by means of magnetic influences.

BRIEF DESCRIPTION OF THE DRAWING

The figure represents a diagram of the execution of the proposed device.

Explanatory Details

Figure 1:
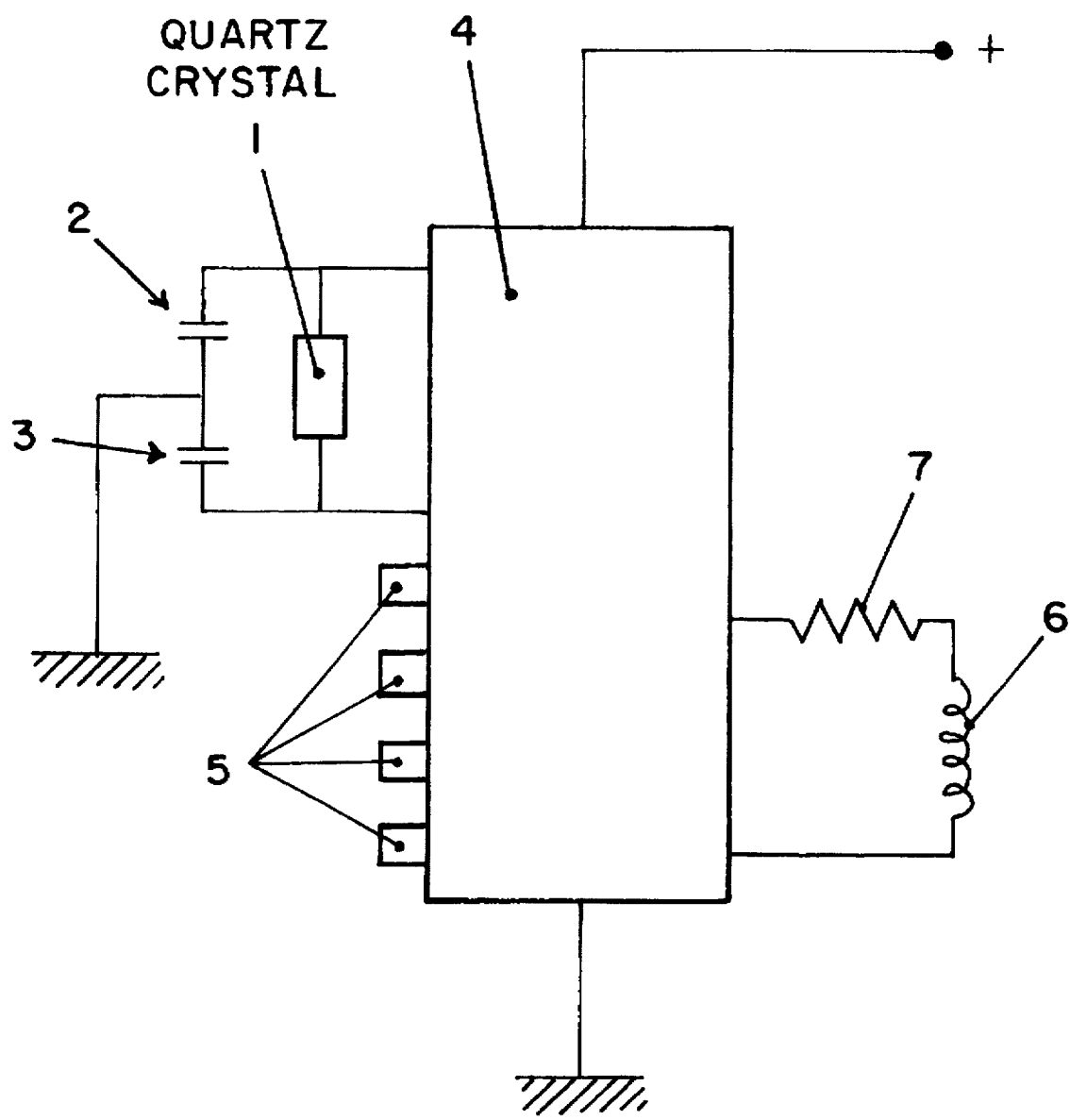

1. Quartz crystal.
2. Capacitor.
3. Capacitor.
4. Microcontroller.
5. Selection contacts.
6. Antenna coil.
7. Limiting resistor.

DESCRIPTION OF THE PREFERRED EMBODIMENTS

The object of the invention refers to an electromagnetic wave generator for influencing the body in the sense of adaptation to concrete biophysical states in a user selectable manner.

For this, said device that is the subject of the invention is composed of a microcontroller (4) and an oscillator circuit, which is formed by a quartz crystal (1) and by a set of respective capacitors (2) and (3). The oscillator circuit (1, 2 and 3) generates the clock frequency for the correct operation of microcontroller (4). In addition, there is a circuit composed of various resistors, represented by limiting resistor (7).

Quartz crystal (1) is anticipated at a frequency of thirty-two kilohertz (32 KHz), since there is no need of an excessive velocity, while allowing for a minimum consumption of current, while capacitors (2) and (3) shall have a range between thirty-three picofarads (33 pF) and sixty-eight picofarads (68 pF).

Said oscillator circuit is incorporated in association with a microcontroller (4) which may be of the PIC16C54 type, which is the lowest in the range of such microcontrollers.

That microcontroller (4) has four pins to which four contacts (5) are applied, by means of which the user may select any of the different frequencies generated by microcontroller (4).

The device is capable of generating waves or oscillations from the hertz to the megahertz range, but the waves that are sought in this case are found in the range that can reach up to thirty hertz (30 Hz), specifically the concrete values of 1.61 Hz, 2.564 Hz, 7.832 Hz, 8.216 Hz and 22.453 Hz, for the frequencies that may be selected by the various contacts (5) of microcontroller (4), so that with the four contacts (5) open the value of 1.61 Hz is selected, and as the four contacts (5) are closed, the remaining four values are selected.

The signals thus generated are diffused through a transmitting antenna, formed by a coil (6), which is coupled at the output of microcontroller (4) by means of current-limiting resistor (7).

The field of influence of the emission is determined by the size of cited antenna (6), which, according to the reduced size of the device, is anticipated to have a design allowing an electric field to be generated that is capable of covering a volume in space of one to two cubic meters, which allows the use of the device both carried by the user and placed close to places of activity or rest.

The various frequencies are selected by means of contacts (5), according to the purpose desired in each case. Together with these contacts (5), formed, by example, by microswitches, there is a conventional switch that is not represented, which plays the role of connector and disconnector to turn the device on and off, so that one of the frequencies is selected when it is turned on, for example, the lowest of the group, leaving the remaining contacts (5) open, while, as contacts (5) are closed, the rest of the frequencies are selected, the on switch having always to be closed for the device to operate.

It has been anticipated that, when the device is turned on, and each time the frequency is changed, operation is indicated for a given time by the lighting of a conventional LED indicator which is not represented, allowing verification of the effectiveness of the operated change, or of the on connection, as the case may be. In addition, if this indicator does not light when connection is made or a change of frequency is carried out, it serves as an indication that the supply pile or battery has run down.

I claim:

1. Perfected wave generator, comprising:

a microcontroller means for generating selected frequencies, an oscillator circuit, coupled to said microcontroller means, including a quartz crystal and two capacitors, a transmitting antenna means formed by a coil, which is coupled to an output of said microcontroller by means of a current-limiting resistor, said transmitting antenna means for transmitting an electromagnetic field to an animal.

2. Perfected wave generator, according to claim 1, wherein the microcontroller has a series of contact switches, by means of which the actuation of the mentioned microcontroller may be selected for the generation of waves of different frequencies between 1 to 30 Hz based on the clock frequency generated by the oscillator circuit.

3. Perfected wave generator, according to claim 2, wherein the microcontroller is provided with a temporary luminous indicator that lights when the generator is turned on and when any of the contact-switches is actuated.

* * * * *